(12) United States Patent
Andrieu et al.

(10) Patent No.: US 7,854,763 B2
(45) Date of Patent: Dec. 21, 2010

(54) INTRAPARIETAL AORTIC VALVE REINFORCEMENT DEVICE AND REINFORCED AORTIC VALVE

(75) Inventors: Raymond Andrieu, Yens (CH); Afksendiyos Kalangos, Geneva (CH)

(73) Assignee: Leman Cardiovascular SA (CH)

( * ) Notice: Subject to any disclaimer, the term of this patent is extended or adjusted under 35 U.S.C. 154(b) by 23 days.

(21) Appl. No.: 10/550,297

(22) PCT Filed: Mar. 8, 2004

(86) PCT No.: PCT/IB2004/000707

§ 371 (c)(1),
(2), (4) Date: Sep. 21, 2005

(87) PCT Pub. No.: WO2004/082537

PCT Pub. Date: Sep. 30, 2004

(65) Prior Publication Data

US 2006/0184239 A1 Aug. 17, 2006

Related U.S. Application Data

(60) Provisional application No. 60/457,291, filed on Mar. 26, 2003.

(30) Foreign Application Priority Data

Mar. 21, 2003 (CH) .................................. 0480/03

(51) Int. Cl.
*A61F 2/24* (2006.01)
(52) U.S. Cl. .................................................... 623/2.4
(58) Field of Classification Search ........ 623/2.11–2.42
See application file for complete search history.

(56) References Cited

U.S. PATENT DOCUMENTS

| 3,983,581 | A | * | 10/1976 | Angell et al. | ............... 623/2.15 |
| 4,247,292 | A |   | 1/1981  | Angell        |                         |
| 4,345,340 | A | * | 8/1982  | Rosen         | ....................... 623/2.19 |
| 4,364,126 | A | * | 12/1982 | Rosen et al.  | ................ 623/2.38 |
| 4,506,394 | A | * | 3/1985  | Bedard        | ....................... 623/2.38 |
| 4,535,483 | A | * | 8/1985  | Klawitter et al. | ............. 623/2.4 |
| 4,666,442 | A | * | 5/1987  | Arru et al.   | ................. 623/2.13 |
| 4,692,164 | A | * | 9/1987  | Dzemeshkevich et al. | .. 623/2.14 |

(Continued)

FOREIGN PATENT DOCUMENTS

EP 0 850 607 7/1998

(Continued)

OTHER PUBLICATIONS

U.S. Appl. No. 11/775,043, Jaffe et al.

(Continued)

*Primary Examiner*—David Isabella
*Assistant Examiner*—Ann Schillinger
(74) *Attorney, Agent, or Firm*—Knobbe Martens Olson & Bear LLP

(57) ABSTRACT

An intraparietal reinforcement device (1) for use in a biological prosthesis (10), as well as a biological prosthesis (10) provided with a device of this type, is particularly suitable for use within the organic tissue of the biological prosthesis (10), and for reinforcing the structure of the prosthesis so that it retains its shape once implanted.

15 Claims, 1 Drawing Sheet

U.S. PATENT DOCUMENTS

Figure 1A:
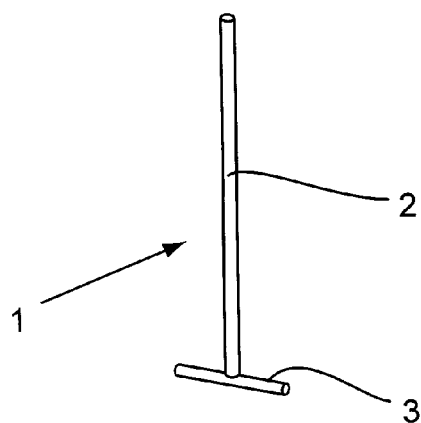

| | | | |
|---|---|---|---|
| 4,755,593 A | | 7/1988 | Lauren |
| 4,851,000 A | * | 7/1989 | Gupta .................. 623/2.18 |
| 5,037,434 A | * | 8/1991 | Lane ................... 623/2.18 |
| 5,178,633 A | * | 1/1993 | Peters .................. 623/2.39 |
| 5,352,240 A | | 10/1994 | Ross |
| 5,549,665 A | * | 8/1996 | Vesely et al. ............ 623/2.14 |
| 5,554,185 A | * | 9/1996 | Block et al. ............. 623/2.12 |
| 5,595,571 A | | 1/1997 | Jaffe et al. |
| 5,713,953 A | * | 2/1998 | Vallana et al. ........... 623/2.15 |
| 5,720,777 A | | 2/1998 | Jaffe et al. |
| 5,843,180 A | | 12/1998 | Jaffe et al. |
| 5,843,181 A | | 12/1998 | Jaffe et al. |
| 5,865,723 A | * | 2/1999 | Love ..................... 600/36 |
| 6,059,827 A | * | 5/2000 | Fenton, Jr. .............. 623/2.17 |
| 6,168,614 B1 | | 1/2001 | Andersen et al. |
| 6,174,331 B1 | * | 1/2001 | Moe et al. .............. 623/2.12 |
| 6,183,512 B1 | * | 2/2001 | Howanec et al. .......... 623/2.36 |
| 6,383,732 B1 | | 5/2002 | Stone |
| 6,461,382 B1 | * | 10/2002 | Cao ..................... 623/2.19 |
| 6,482,228 B1 | * | 11/2002 | Norred .................. 623/2.17 |
| 6,558,418 B2 | | 5/2003 | Carpentier et al. |
| 6,761,735 B2 | | 7/2004 | Eberhardt et al. |
| 6,767,362 B2 | * | 7/2004 | Schreck ................. 623/2.11 |
| 7,044,966 B2 | | 5/2006 | Svanidze et al. |
| 7,172,625 B2 | | 2/2007 | Shu et al. |
| 7,247,167 B2 | | 7/2007 | Gabbay |
| 7,323,010 B2 | * | 1/2008 | Verona et al. ........... 623/2.14 |
| 7,399,315 B2 | | 7/2008 | Iobbi |
| 7,556,645 B2 | | 7/2009 | Lashinski et al. |
| 7,618,447 B2 | | 11/2009 | Case et al. |
| 2001/0039450 A1 | * | 11/2001 | Pavcnik et al. ........... 623/1.24 |
| 2003/0023302 A1 | * | 1/2003 | Moe et al. ............... 623/2.4 |
| 2004/0098098 A1 | * | 5/2004 | McGuckin et al. ........ 623/1.14 |
| 2005/0075724 A1 | | 4/2005 | Svanidze et al. |
| 2005/0075726 A1 | | 4/2005 | Svanidze et al. |
| 2007/0288087 A1 | | 12/2007 | Fearnot et al. |
| 2008/0243246 A1 | | 10/2008 | Ryan et al. |

FOREIGN PATENT DOCUMENTS

| | | |
|---|---|---|
| WO | WO 96/40008 A1 | 12/1996 |
| WO | WO 00/67661 | 11/2000 |
| WO | WO 01/30275 | 5/2001 |
| WO | WO 2006/092648 | 9/2006 |
| WO | WO 2008/035337 A2 | 3/2008 |
| WO | WO 2008/150529 A1 | 12/2008 |

OTHER PUBLICATIONS

U.S. Appl. No. 11/814,155, Andrieu et al.
International Search Report for International Application No. PCT/IB2004/000707, dated Jun. 30, 2004.
International Search Report for International Application No. PCT/IB2005/000573, dated Dec. 14, 2005.
Preliminary Amendment for U.S. Appl. No. 11/814,155, dated Jul. 17, 2007, in 6 pages.
Office Action dated June 16, 2009, from Application No. 2008-0133005 filed Jul. 17, 2007.
Interview Summary dated Oct. 23, 2009 in U.S. Appl. No. 11/814,155, filed Jul. 17, 2007.
Office Action dated Dec. 31, 2009 in U.S. Appl. No. 11/755,043, filed Jul. 9, 2007.
Invitation to Pay Additional Fees and Partial International Search Report dated Feb. 11, 2010 in International Application No. PCT/US2008/069344.
Final Office Action dated Feb. 17, 2010 in U.S. Appl. No. 11/814,155, filed Jul. 17, 2007.
Response filed on Mar. 2, 2010 in U.S. Appl. No. 11/755,043, filed Jul. 9, 2007.
Notice of Allowance dated Apr. 19, 2010 in U.S. Appl. No. 11/755,043, filed Jul. 9, 2007.

* cited by examiner

INTRAPARIETAL AORTIC VALVE REINFORCEMENT DEVICE AND REINFORCED AORTIC VALVE

This invention relates to an intraparietal reinforcement device that is designed to be integrated in a biological prosthesis as well as a biological prosthesis that is equipped with such a device.

Cardiac surgery knows a constant development due to the technical advancement as regards equipment and techniques used. In particular, the valvular prostheses for the heart form the subject of research, and several types of these prostheses are currently available.

First of all, mechanical prostheses are known that consist essentially of a metal part that comprises a cage and flaps that constitute the actual valve itself as well as a ring that is made of synthetic material such as Teflon that makes it possible to make the device integral with the periphery of the orifice that is to be replaced. Despite its significant service life, this type of prosthesis has a considerable number of drawbacks, in particular the necessity for anticoagulating treatment of the patient for his entire life.

There are also biological prostheses that make it possible, i.a., to eliminate this anticoagulating treatment. They are often animal valves taken essentially from pigs and then treated by a suitable process so as to prepare them for implantation in the human body. Currently, it is possible to group these biological prostheses into two different categories, stented prostheses, on the one hand, and unstented prostheses, on the other hand.

The first named prostheses consist of a biological valve, for example the porcine aortic valve or a biological valve that is reconstructed from a bovine pericardium, and a rigid ring. This ring is made of a suitable material such as titanium covered by a material such as Teflon and surrounds the valve to which it is attached. It thus is used, on the one hand, as a support of the biological valve so as to keep it in place and in its shape once implanted, and, on the other hand, as an anchoring point on which are placed the suture points that attach the stented biological prosthesis to the orifice that is to be equipped with the valve. The ring is thus an artificial intermediate element between the natural walls of the orifice and the implanted biological valve. By its design, it therefore makes it possible to carry out the implantation of the biological prosthesis that is prepared in advance in a simplified way in the sense that it requires only a single level of suture around its periphery at the level of the ring of the native valve to be replaced, whereby the biological prosthesis is attached and kept in place by this support, the stent. In contrast, except for allowing this relatively simple and advantageous implantation technique, the presence of this ring also brings about significant drawbacks, in particular, due to the fact that the biological prosthesis that comprises this rigid ring as a stent is placed in the natural orifice, the space that is available for the replacement valve is reduced relative to the original human valve by the surface area of the circumference that is occupied by the stent. Consequently, the pressure gradient in the replacement valve is artificially increased by the presence of the stent.

Thus, unstented biological prostheses that comprise only a synthetic material, such as Teflon that is sewn around its periphery during the process of preparation of such a prosthesis or a biological tissue such as the pericardium that is treated in advance, are also now used. These two types of materials occupy appreciable less volume than a stent of the type that is described above. The pressure gradient in the replacement valve thus more resembles the natural value.

Because of the increased flexibility of this type of biological prosthesis relative to the stented biological prostheses as well as relative to mechanical prostheses, it also offers an advantage in terms of hemodynamics through the orifice that is equipped with the replacement valve. In contrast, these advantages are counterbalanced by the fact that the complexity of the technique and therefore the time of implanting such an unstented prosthesis are considerably increased. Actually, the absence of a stent that keeps the biological valve in place and gives it the necessary stability requires the surgeon to place, during implantation, an additional suture around the periphery of the valve in subcoronary position. In addition, the biological prosthesis should be implanted, for example in the case of a replacement of the aortic valve, in a specific orientation that is hard for the surgeon to see because it is located inside the natural orifice. If the rigid structure of the stent can be used in the case of a stented biological prosthesis as a means for marking the necessary orientation, the implantation is made all the more difficult in the case of unstented biological prostheses because of the absence of this marking.

The object of this invention is to prevent the above-mentioned drawbacks of the current means and to create a reinforcement device for biological prostheses making possible the production of biological prostheses that simultaneously combine the advantages of stented and unstented conventional biological prostheses, in particular to produce biological prostheses that are stiffened and kept in their desired shape without resorting to a traditional stent and that use maximum surface area and available volume for their primary function, while being able to apply the relatively simple and quick implantation technique of current stented biological prostheses to this new type of reinforced biological prostheses.

Thus, the subject of this invention is an intraparietal reinforcement device for biological prostheses comprising the characteristics disclosed herein, whereby the device is suitable in particular for being placed inside the organic tissue of this biological prosthesis and for reinforcing the structure of the latter so as to keep its shape after implantation, as well as biological prostheses that are equipped with at least one device of this type.

The device comprises in particular an intraparietal rod that is suitable for being inserted in the organic tissue of the biological prosthesis and a leg that is attached to a first end of the rod.

By these measures, a device is obtained that is suitable for imparting adequate stability and rigidity to a biological prosthesis to keep it in its desired shape, without resorting to a bulky conventional stent, whereby the pressure gradient in the replacement valve is, because of the increased available surface area, more comparable to the preliminary natural state and thereby extends the service life of the biological prosthesis, as for an unstented biological prosthesis, while opening up the possibility of transferring the favorable implantation technique of stented biological prostheses to the new type of biological prostheses thus created.

Other advantages emerge from characteristics expressed in the dependent claims and from the description, which here beneath discloses more details of the invention with drawings.

Schematically and by way of example, the attached drawings illustrate several embodiments of the invention.

Figure 1B:
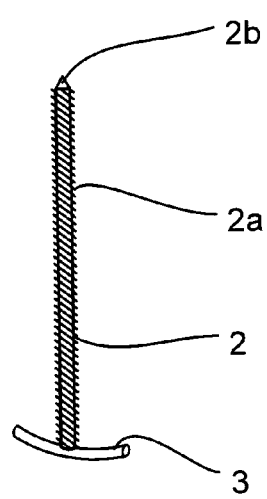
Figure 1C:
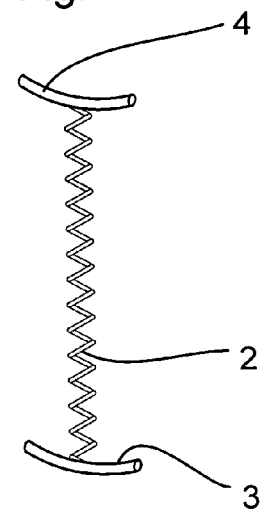

FIGS. 1a-c schematically illustrate the principle and three different embodiments of an intraparietal reinforcement device for biological prostheses.

Figure 2:
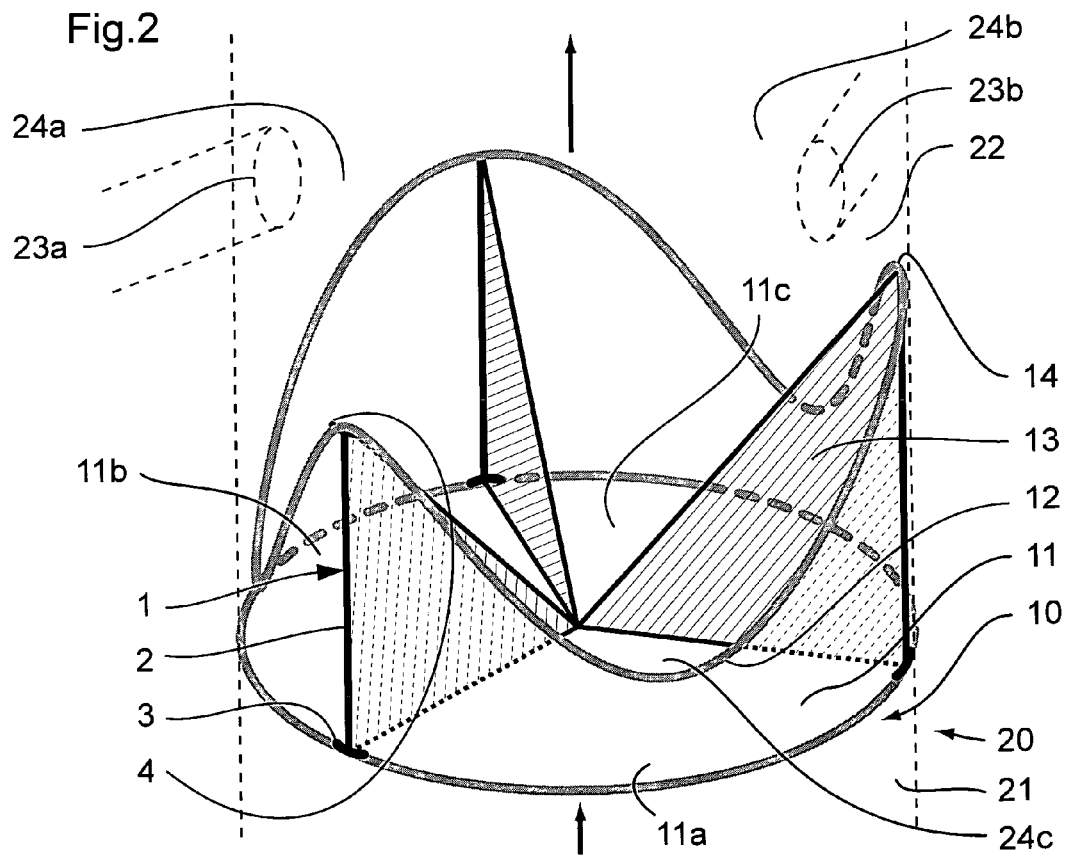

FIG. 2 is a schematic view of a biological prosthesis that is equipped with intraparietal reinforcement devices and that is placed, by way of example, between the root of the aorta and the ascending aorta.

The invention will now be described in detail with reference to the attached drawings. The description will refer, by way of example and so as to simplify the explanations, but without limiting the application of this invention to this specific case, in particular to a biological prosthesis that is reinforced with devices according to the invention and that is particularly suitable for the replacement of the aortic valve of the heart.

This same valve can also be implanted in mitral position or tricuspid position provided that it is in harmony with the direction of blood flow.

FIG. 1 shows a first embodiment of an intraparietal reinforcement device 1 that is designed to be integrated into a biological prosthesis according to this invention. This device comprises a central portion that is realized by an intraparietal rod 2 that is suitable for being inserted into the organic tissue of the biological prosthesis and a first end part that is realized by a leg 3 that is attached perpendicularly to the central portion at a first end of rod 2. The device, at the very least its central portion, is therefore suitable for being placed inside the organic tissue of a biological prosthesis and thus makes it possible to reinforce the structure of the latter so as to keep its shape after implantation.

The central portion of device 1 can be, as FIG. 1a shows, formed by a straight and simple rod 2. It can also take the shape of an intraparietal rod 2 that has on its surface a helical portion 2a in the shape of a thread, as shown in FIG. 1b. This central portion could also be shaped by a rod 2 with a helical shape so as to form a "miniature corkscrew," as is illustrated schematically in FIG. 1c. These last two variants are advantageous because they allow to stabilize device 1 in the position in which it was introduced into the tissue of the biological prosthesis.

In the second end opposite to the first end that carries above-mentioned leg 3, rod 2 can comprise a pointed portion 2b that is suitable for piercing and for penetrating, without causing damage, the organic tissue of the biological prosthesis. This case is, by way of example, illustrated in FIG. 1b, but the embodiments of FIGS. 1a and 1c can also comprise this characteristic that facilitates the insertion of the intraparietal reinforcement device 1 into the organic tissue of the biological prosthesis.

As FIG. 1c shows, the device can also comprise a second end portion in the form of an attachment 4 that is suitable for being attached to the second end of its central portion. In particular in the case where the second end comprises a pointed portion 2b, this attachment acts as a cap so as to cover this pointed portion 2b and to ensure the stability of device 1 in the position in which it was introduced into the organic tissue of the biological prosthesis. Attachment 4 can be straight or can be a curved bar, whereby the curve corresponds to the curvature of the outside circumference of the biological prosthesis at the plane of intersection where the attachment is to be placed.

The same comment applies to leg 3 that is attached to the first end of the central portion of the device, which can be simply a straight bar or a curved bar, whereby the curvature corresponds to the curvature of the outside circumference of the biological prosthesis at the plane of intersection where leg 3 is to be placed, which normally corresponds, in the above-mentioned case, of a biological prosthesis for an aortic valve or a mitral valve, or a tricuspid valve, approximately to the plane in which this valve is located.

The intraparietal reinforcement device 1 is made of a material that is suitable for ensuring adequate stability while having a certain flexibility, such as a flexible and/or semi-rigid and/or rigid polymer, or a flexible metal such as titanium.

After having described device 1 as such, a detailed description of an example of a biological prosthesis that is reinforced with this type of device will now follow, with reference to FIG. 2. This figure shows a schematic view of a biological prosthesis for the replacement of aortic valve 10 that is equipped with intraparietal reinforcement devices 1 according to this invention and placed in the aorta 20, between the root of the aorta 21 and the ascending aorta 22.

As shown in FIG. 2, the biological prosthesis for the replacement of above-mentioned aortic valve 10 is equipped with at least one intraparietal reinforcement device 1 of an embodiment described above and in the specific case of preferably three devices 1. Regarding the biological portion of prosthesis 10, it involves in most cases a porcine aortic valve that is equipped, during a preliminary treatment before implantation, with intraparietal reinforcement devices 1.

The arrangement of intraparietal reinforcement device 1 and its location in the reinforced biological prosthesis is readily understood in view of the natural structure of the porcine aortic valve to be equipped corresponding to the human valve to be replaced. This aortic valve and the biological prosthesis, shown schematically in FIG. 2, essentially comprise three layers 11a, 11b, and 11c that form the plane of the valve, a tubular outside wall 12 that originally forms part of the tubular wall of the animal aorta and surrounds the plane that is formed by the layers, whereby the latter are integral with this tubular outside wall 12 at their outside end, as well as for each of layers 11a, 11b and 11c essentially triangular vertical walls that are called commissures 13 that extend towards the center of the valve or the cardiac cavity for the mitral or tricuspid positions and that are integral, on the one hand, with the two ends of layers 11a, 11b and 11c that are oriented to the inside of the valve or the cardiac cavity for the mitral or tricuspid positions and, on the other hand, the tubular outside wall 12. Thus, the flow of the blood can be propagated in the direction from the root of the aorta 21 towards the ascending aorta 22 or from the auricle towards the ventricular cavity, as indicated by the arrows in FIG. 2, while this is not possible in the opposite direction. The porcine aortic valve that is used as the biological portion of the reinforced biological prosthesis 10 is taken from the animal aorta and, in the case of a replacement of the aortic valve that is described here by way of example, the tubular outside wall 12 is normally cut into a sinusoidal form so as, on the one hand, to integrate the sino-tubular junctions 14 that correspond to the highest contact points between the tubular outside wall 12 and the commissures 13 relative to the plane of the valve and, on the other hand, to provide space for the right coronary artery 23a or the left coronary artery 23b that comes out at the right Valsalva sinus 24a or at the left Valsalva sinus 24b. The portion of this wall 12 opposite the non-coronary Valsalva sinus 24c can also comprise a sinusoidal form.

Given this natural configuration of the aortic valve, intraparietal rod 2 of intraparietal reinforcement devices 1 is placed inside tubular outside wall 12 of the valve along the lines of intersection of this wall with the commissures 13 of the valve. This arrangement is illustrated in FIG. 2, where leg 3 of device 1 is placed in the lower portion of the prosthesis in the plane of the valve, a point that is also used as a point of insertion of the device into the tissue of the biological prosthesis, and attachment 4 is, if necessary, placed approximately at the level of the sino-tubular junction 14. The length of the central portion of device 1 depends on the size of the aortic, mitral or tricuspid valve that is to be installed and is normally between 3 and 30 mm. It can be selected so as to correspond to the length of the line of intersection of the commissures 13 with the tubular outside wall 12 of the valve, can be slightly longer so as to exceed by several millimeters the sino-tubular junction 14 or can also be slightly shorter. Leg 3 and attachment 4 extend laterally and perpendicularly from rod 2 by about 1 to 4 mm so as to go along the peripheral circumference of biological prosthesis 10. The thickness of the parts of the device is several tenths of a millimeter. The intraparietal reinforcement devices 1 thus make it possible to impart adequate stability to the porcine aortic valve and in particular commissures 13 and the tubular outside wall 12 in order to keep their shape after implantation.

Leg 3 and/or, if present, attachment 4 of intraparietal reinforcement devices 1 are/is covered by a Teflon material, as can be the entire outside periphery of the tubular outside wall 12 of the reinforced biological prosthesis 10. The first measure makes it possible, i.a., to ensure the separation of parts of the intraparietal reinforcement device 1 from the bloodstream; the second measure makes it possible to use a large surface area for anchoring of the suture that is applied during the implantation of the reinforced biological prosthesis 10 in the human body.

An intraparietal reinforcement device according to this invention can be used for any biological prosthesis that requires its reinforcement by means that occupy the least space possible so as to use this space for its primary function, like the valvular function in the example that is described above, and its application is therefore not limited to this example of a biological prosthesis for the replacement of the sigmoid valve of the aorta, the mitral valve or the tricuspid valve.

Thus, a biological prosthesis 10 that is reinforced with an intraparietal reinforcement devices 1 makes it possible, by its design, to carry out the implantation of biological prosthesis 10, prepared and installed in advance, in a relatively quick and simple way in the sense that it requires only a single suture around its periphery at the level of the valve ring, whereby the latter and in particular the commissures 13 are stiffened and kept in place by devices 1, analogously to the case of the stented biological prostheses. Since the biological prosthesis is to be implanted, primarily in the case of a replacement of the aortic valve, in a specific orientation that is hard for the surgeon to see because it is located inside the natural orifice, the intraparietal reinforcement devices 1 can also be used as a means of reference for the necessary orientation, thus facilitating the implantation. In addition, the space available for the replacement valve is similar to that of the original human valve because of the absence of a bulky rigid structure like the conventional stent. Consequently, the pressure gradient in the replacement valve is also similar to its natural value, instead of being artificially increased by the presence of a stent. In addition, because of the flexibility of such a reinforced biological prosthesis relative to the stented biological prostheses as well as relative to the artificial prostheses, it offers an advantage in terms of the hemodynamics through the orifice that is equipped with this replacement valve.

This invention therefore allows to create an intraparietal reinforcement device for biological prostheses that make possible the production of biological prostheses that simultaneously combine the advantages of conventional stented and unstented biological prostheses, in particular to produce biological prostheses that are stiffened and kept in their desired shape without resorting to a traditional stent and are using a maximum of the surface area and of the volume available for their primary function, while enabling to transfer the relatively simple and quick technique of implanting current stented biological prostheses to this new type of reinforced biological prostheses.

The invention claimed is:

1. A biological prosthesis comprising a substantially intact aortic valve obtained from an animal, through which substantially intact aortic valve blood flows in a single direction, the substantially intact aortic valve having a tubular outer wall, and at least one intraparietal reinforcement device comprising a rod implanted in said tubular outer wall of said substantially intact aortic valve, the rod penetrating the thickness of the tubular outer wall of said substantially intact aortic valve and extending substantially parallel to said direction of blood flow.

2. A biological prosthesis according to claim 1, there being a plurality of said intraparietal reinforcement devices implanted in said outer tubular wall of said substantially intact aortic valve, in spaced relation to each other.

3. A biological prosthesis according to claim 2, wherein said intraparietal reinforcement devices are parallel to each other.

4. A biological prosthesis according to claim 1, wherein said substantially intact aortic valve has commissures that are parallel to said direction and perpendicular to said tubular wall of said substantially intact aortic valve and joined to said tubular wall of said substantially intact aortic valve, said intraparietal reinforcement device being implanted at the juncture of said outer tubular wall of said substantially intact aortic valve and a said commissure.

5. A biological prosthesis according to claim 4, wherein said substantially intact aortic valve has three said commissures and there is a said intraparietal reinforcement device implanted at the juncture of each said commissure with said tubular outer wall of said substantially intact aortic valve.

6. A biological prosthesis according to claim 5, said intraparietal reinforcement devices being spaced apart from each other.

7. A biological prosthesis according to claim 1, wherein said intraparietal reinforcement device is covered with a fluoropolymer material.

8. A biological prosthesis according to claim 1, wherein said intraparietal reinforcement device is straight.

9. Previously presented) A biological prosthesis according to claim 1, wherein said intraparietal reinforcement device has a helical shape.

10. A biological prosthesis according to claim 1, wherein said intraparietal reinforcement device has a helical surface portion.

11. A biological prosthesis according to claim 1, wherein said intraparietal reinforcement device has a pointed end.

12. A biological prosthesis according to claim 1, wherein said intraparietal reinforcement device has a cross piece at one end.

13. A biological prosthesis according to claim 12, wherein said cross piece is a straight bar.

14. A biological prosthesis according to claim 12, wherein said cross piece has the same curvature as said tubular wall of said substantially intact aortic valve.

15. A biological prosthesis according to claim 12, wherein there is a cross piece at each end of the intraparietal reinforcement device.

* * * * *

UNITED STATES PATENT AND TRADEMARK OFFICE
CERTIFICATE OF CORRECTION

PATENT NO. : 7,854,763 B2
APPLICATION NO. : 10/550297
DATED : December 21, 2010
INVENTOR(S) : Andrieu et al.

Page 1 of 1

It is certified that error appears in the above-identified patent and that said Letters Patent is hereby corrected as shown below:

In Column 6, Line 45, in Claim 9, before "A" please delete "Previously presented)".

Signed and Sealed this
Ninth Day of August, 2011

David J. Kappos
*Director of the United States Patent and Trademark Office*